United States Patent [19]

Greenberg

[11] Patent Number: 5,133,720
[45] Date of Patent: Jul. 28, 1992

[54] SURGICAL DRILL GUIDE AND RETRACTOR

[76] Inventor: Alex M. Greenberg, 145 W. 67th St., New York, N.Y. 10023

[21] Appl. No.: 719,178

[22] Filed: Jun. 21, 1991

Related U.S. Application Data

[63] Continuation-in-part of Ser. No. 552,703, Jul. 13, 1990, Pat. No. 5,026,376.

[51] Int. Cl.$^5$ ............................................. A61B 17/00
[52] U.S. Cl. ....................................... 606/96; 606/86
[58] Field of Search ...................... 606/79, 80, 86, 96, 606/97, 98, 102, 104

[56] References Cited

U.S. PATENT DOCUMENTS

| | | | |
|---|---|---|---|
| 2,427,128 | 9/1947 | Ettinger | 606/86 |
| 2,494,229 | 7/1948 | Collison | |
| 3,752,161 | 8/1973 | Bent | 606/79 X |
| 3,835,860 | 9/1974 | Garretson | 606/79 |
| 4,586,497 | 5/1986 | Dapra et al. | 606/79 X |
| 4,739,751 | 4/1988 | Sapega et al. | |
| 4,813,407 | 3/1989 | Vogen | 606/86 |
| 4,883,048 | 11/1989 | Purnell et al. | |
| 5,026,375 | 6/1991 | Linovitz et al. | 606/79 |

FOREIGN PATENT DOCUMENTS

| | | | |
|---|---|---|---|
| 6455252 | 7/1962 | Canada | |
| 2903471 | 8/1979 | Fed. Rep. of Germany | 606/80 |
| 2598311 | 5/1988 | France | |
| 649420 | 2/1979 | U.S.S.R. | 606/79 |

OTHER PUBLICATIONS

Oral and Maxillofacial Traumatology, "Internal Fixation of Zygomatic and Midface Fractures by Means of Miniplates and Lag Screws", pp. 177-186 Quintessence Publishing Co., Inc. 1986.

*Primary Examiner*—Robert A. Hafer
*Assistant Examiner*—Sam Rimell
*Attorney, Agent, or Firm*—Marmorek, Guttman & Rubenstein

[57] ABSTRACT

A combined surgical drill guide and retractor is useful for treating fractures in the craniomaxillofacial region. The device comprises an L-shaped member having a first short leg and a second long leg, a major retractor extending away from the first leg in a first direction and a minor retractor extending away from the first leg in an opposite direction, an outer sleeve mounted on the first leg, an inner sleeve telescoped within the bore of the outer sleeve, and a lever hingedly mounted on the second leg of the L-shaped member for carrying out a scissoring movement in cooperation with the second leg. The major retractor and the minor retractor cooperate so that when they are inserted into an incision, they will retract the sides of the incision. The major retractor has an arcuate C-like shape so that it can extend around and behind a bone and thus act as a protective stop to prevent a drill bit from penetrating beyond the bone being drilled. The inner sleeve is slidable between a first retracted position and a second extended position to press against a template. The lever is mounted for scissoring movement on the second, long leg of the L-shaped member. When one end of the lever is pressed towards the long leg of the L-shaped member, the other end of the lever forces the inner sleeve to slide forward into its extended position up against a template in place along a reduced bone structure. After the holes are drilled, the template is fixed in place by surgical screws inserted into the holes.

15 Claims, 9 Drawing Sheets

SURGICAL DRILL GUIDE AND RETRACTOR

This is a continuation-in-part of application Ser. No. 07/552,703, filed Jul. 13, 1990, now U.S. Pat. No. 5,026,376, issued Jun. 25, 1991.

BACKGROUND OF THE INVENTION

The invention relates to a combination surgical drill guide and retractor. More particularly, the invention relates to a surgical instrument which simultaneously retracts the skin at the sides of an incision and acts as a drill guide for the surgical drilling of anatomical bone. The inventive device is particularly useful for the treatment of bone fractures in the zygomaticofrontal and infraorbital rim regions.

The treatment of bone fractures in the craniomaxillofacial region generally proceeds by reducing the fractured bones to their anatomically correct positions, and thereafter fixing the bones in place. The bones may be fixed into place either by interosseous wiring, or by the technique of miniplate osteosynthesis. Particularly in the case of zygomatic fractures, interosseous wiring may not provide stable fixation. On the other hand, miniplate osteosynthesis is capable of providing rigid internal fixation in the mid-face region, and is the clearly preferred technique in the case of zygomatic, or cheek bone fractures requiring fixation after reduction.

Miniplate osteosynthesis for mid-face fractures proceeds as follows. An incision is made in the region of the fracture, the skin is retracted, and the bones are reduced to their correct anatomical positions. A miniplate or template is then positioned onto the reduced bone structure. The miniplate contains a number of countersunk holes which are designed to receive surgical screws. While the miniplate is held in place on the reduced bone structure, a drill bit is inserted through the holes of the miniplate and the bone structure is drilled in line with the holes of the miniplate. Thereafter, the drill bit is removed and self-tapping screws are screwed through the miniplate and the bone structure. The miniplate is thereby fixed into place and holds the bone structure together so that it can heal.

It is of course apparent that in drilling the holes in the bone structure, the surgeon does not wish to drill too deeply into the orbital region. Complications, such as blindness, extraocular muscle dysfunction, retinal damage, and severe trauma could result if the depth of holes is not gauged accurately. Accordingly, it is desirable during this drilling procedure to use an instrument which will prevent the surgeon from drilling too deeply into the ocular region.

Heretofore, a special orbital drill guide has been proposed for use in performing miniplate osteosynthesis in the orbital margin. (See, e.g., FIGS. 10.4-6, appearing on page 181 of Krüger et al, *Oral and Maxillofacial Traumatology*, Vol. 2, Quintessence Pub. Co., Inc., Chicago (1986)). The special orbital drill guide consists of a handle, a curved C-shaped arm attached to the handle, and a plunging mechanism also attached to the handle. The plunging mechanism consists of an outer sleeve and an inner sleeve, each of which has a through-going bore. The inner sleeve is slidably mounted within the outer sleeve, whereby it functions as a plunger. Both inner and outer sleeves are mounted on the handle in line with the C-shaped member.

To employ the special orbital drill guide, an assistant uses malleable retractors to retract the sides of the incision. With the surgeon holding the drill guide by the handle, the C-shaped arm is inserted into the incision and manipulated until it is positioned on and behind the orbital bone. The tip of the C-shaped arm is thus able to act as a protective stop behind the bone to be drilled. The outer sleeve is aligned with one of the holes in the miniplate and the inner sleeve is plunged forward through the outer sleeve until it comes in contact with a hole of the miniplate. Thereafter, a drill bit is inserted through the bore of the inner sleeve and a hole is drilled through the orbital bone in line with the hole of the miniplate. The tip of the C-shaped arm prevents the drill bit from penetrating too deeply into the ocular region.

The special orbital drill guide described above, while useful, is not entirely satisfactory for the described procedure. First, the special orbital drill guide, particularly its plunging mechanism, is difficult to manipulate and keep in place when drilling bones. Second, the C-shaped arm is not very well adapted to go around the orbital bone and act as a protective stop. The arm is too narrow to act as a retractor and its hemispherical shape extends too far into the orbit creating pressure on the eyeball which can cause contusion of extraocular muscles and retinal detachment. Third, the special orbital drill guide does not include any mechanism to retract the contra-lateral side of the incision. Since one of the surgeon's hands will be needed to hold the drill guide in place and the other hand will be needed to perform the actual drilling, an assistant will be required to retract the incision.

Accordingly, it is an object of the present invention to provide a combined surgical drill guide and retractor which will simultaneously act as a drill guide for drilling anatomical bones and also retract the sides of an incision.

It is another object of the present invention to provide a combined surgical drill guide and retractor which is easily manipulable with one hand.

It is yet another object of the present invention to provide a combined surgical drill guide and retractor in which a protective stop is contoured more closely to the shape of the orbital bone in order to lessen pressure on the eyeball.

SUMMARY OF THE INVENTION

These and other objects are achieved by means of the combined surgical drill guide and retractor described herein which comprises an L-shaped member having a first short leg and a second long leg, a major retractor extending away from the first leg in a first direction and a minor retractor extending away from the first leg in an opposite direction, an outer sleeve mounted on the first leg, an inner sleeve telescoped within the bore of the outer sleeve, and a lever hingedly mounted on the second leg of the L-shaped member for carrying out a scissoring movement in cooperation with the second leg.

The major retractor and the minor retractor extend away from the first leg of the device in opposite directions so that when they are inserted into an incision, they will retract the sides of the incision. The major retractor has an arcuate C-like shape so that it can extend around and behind the orbital bone and thus act as a protective stop to prevent a drill bit from penetrating into the ocular region too deeply. Desirably, the tip of the major retractor behind the bone is somewhat concave so that it presses against the ocular bone and slopes away from the eyeball. Desirably too, the minor retractor is bifurcated so that it can pass around any major nerves in the region without disturbing them. In addition, in particular embodiments the major retractor may be contoured on its lateral aspects or bifurcated at its tip to avoid injury to certain anatomical structures, specifically the lateral canthal ligament and its insertion at Whitnalls tubercle.

The inner sleeve is slidably mounted within the through-going bore of the outer sleeve to move between a first retracted position and a second extended position wherein the inner sleeve passes through a bore in the major retractor and into contact with a miniplate. Desirably, a resilient spring is mounted on the inner sleeve and biases it towards its retracted position.

The lever is mounted by means of a hinge onto the second, long leg of the L-shaped member. The mounting is such that a scissoring movement is effected. Thus, when one end of the lever is pressed towards the long leg of the L-shaped member, the other end of the lever forces the inner sleeve to slide forward into its extended position up against the miniplate. Thereafter, drilling can proceed as previously described.

In addition to acting as a combined retractor and drill guide and being highly manipulable, the device of the present invention has the added advantage of acting as a clamp to hold the miniplate in position and also serves to hold the fractured bones in their correct positions. Because the tip of the inner sleeve is beveled, it fits into the holes of the miniplate and prevents it from shifting during drilling.

In order to increase the versatility of the device, the minor retractor may be attached to the short leg by a universal joint which will allow adjustment of its position.

DETAILED DESCRIPTION OF THE INVENTION

Figure 1:
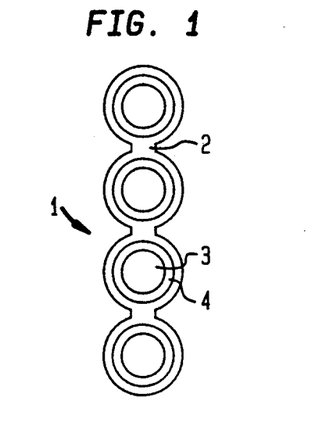
FIG. 1 illustrates a miniplate which is used in conjunction with the combined drill guide and retractor of the present invention.

Referring to FIG. 1, a greatly enlarged miniplate 1 which is useful in the treatment of zygomatic and infraorbital fractures is shown. Numerous different configurations of the miniplate may be used depending on the size and shape of the reduced bone structure. Miniplate 1 is just one example of a suitable miniplate. The miniplate 1 consists of a chain-like body 2 having holes 3 therein. Each of the holes 3 is countersunk with a beveled edge 4 so that the holes 3 are adapted to receive surgical screws (not shown) and to retain the reduced bone structure in place until the bone heals.

Figure 2A:
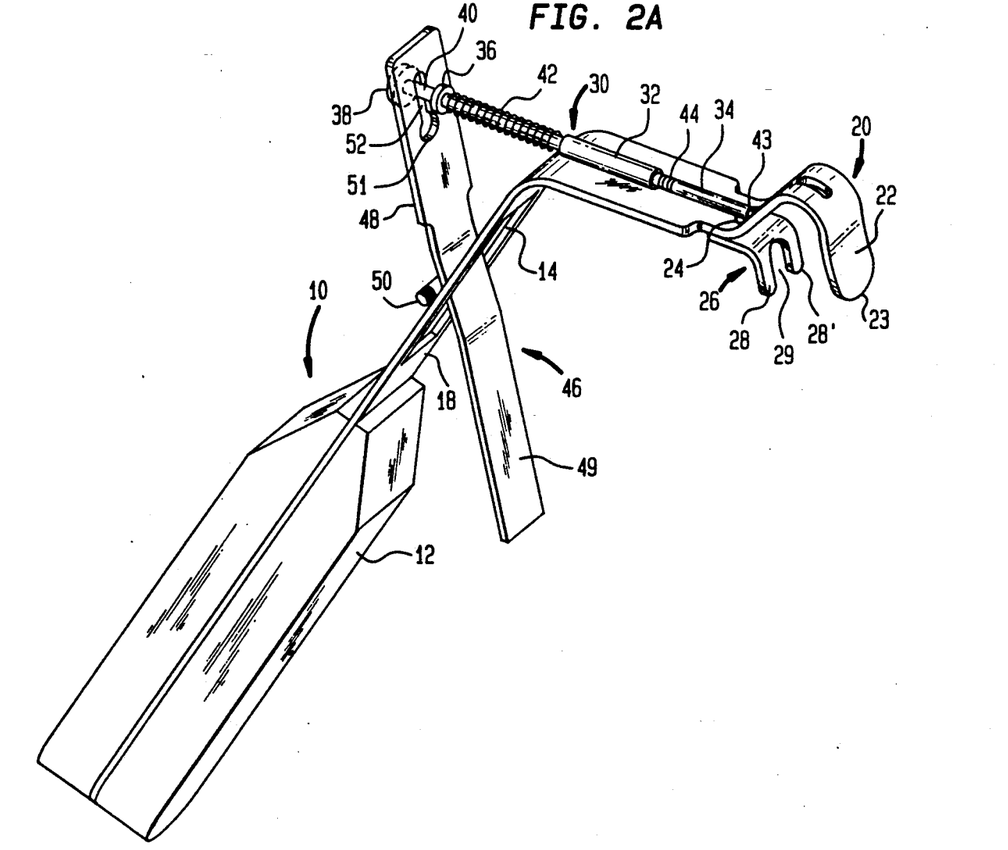
FIGS. 2A and 2B illustrate one embodiment of the inventive surgical drill guide and retractor.
Figure 2B:
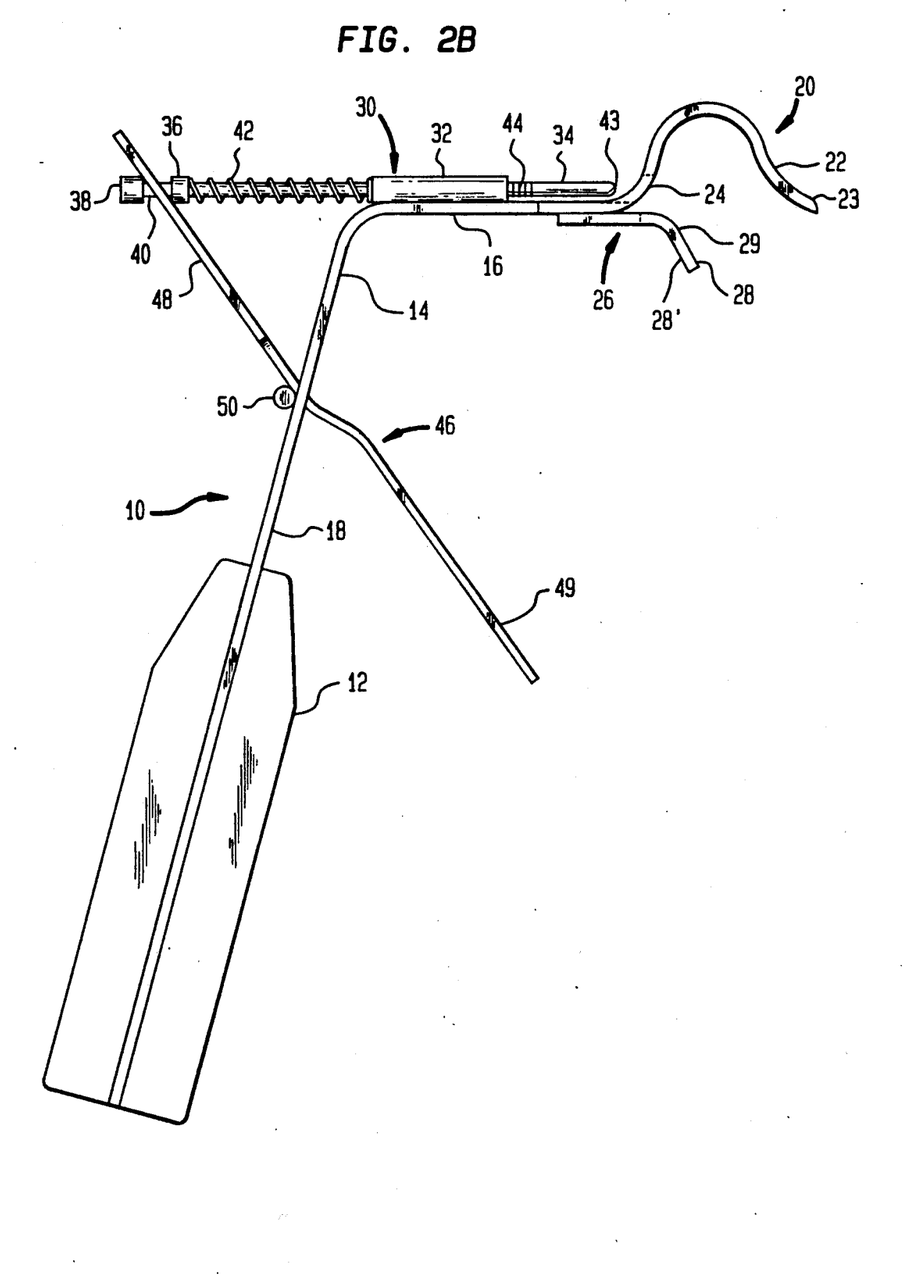

Referring now to FIGS. 2A and 2B, an embodiment of the inventive surgical drill guide and retractor is illustrated. The surgical drill guide and retractor 10 comprises a handle 12 from which a substantially L-shaped member 14 extends. The L-shaped member has a first short leg 16 and a second long leg 18. The long leg 18 extends from handle 12.

The end of the short leg 16 terminates in an arcuate member which constitutes the major retractor 20. In the embodiment shown in FIG. 2, the major retractor 20 is integral with and extends from the short leg 16 although this need not be so. It may also be a separate piece which is attached by welding to the short leg 16. As illustrated, the major retractor 20 is about $\frac{1}{8}''$ wide, arcuate in shape, and has a slight concavity 22 near its tip 23. This shape allows the major retractor to be inserted around and behind a bone where it rests securely. This shape also results in the major retractor 20 being sloped away from the eyeball, thus putting less pressure on the eyeball itself. At the end of the major retractor 20 where it extends from the short leg 16, the major retractor 20 has an aperture 24, the purpose of which will be apparent later.

A minor retractor 26 also extends from the short leg 16 at approximately the same location as the major retractor 20. The minor retractor 26 is welded to the bottom of leg 16 as illustrated, or may be attached by means of a universal joint (not shown) which permits adjustment of its position. The minor retractor 26 extends in a direction substantially opposite to the initial direction of major retractor 20. When inserted into an incision, the major retractor 20 and minor retractor 26 cooperate so as to provide an opening effect thereby retracting the sides of the incision. The minor retractor 26 is much shorter than major retractor 20 and bifurcated resulting in the fingers 28, 28' separated by the bifurcation 29. The purpose of this structure is to enable the minor retractor 26 to be inserted around any nerves which might be located in the region of the incision.

Mounted on top of the short leg 16 is a plunging mechanism 30. The plunging mechanism 30 comprises an outer sleeve 32 and an inner sleeve 34. Each of these sleeves has a through-going, longitudinal bore. The inner sleeve 34 is telescoped within the through-going bore of outer sleeve 32 so that it may slide in the longitudinal direction within outer sleeve 32. At one end of the inner sleeve 34, there are two circumferential shoulders 36 and 38 with a circumferential land 40 between them. A coil spring 42 is disposed between an edge of outer sleeve 32 and the shoulder 36 in order to resiliently bias the inner sleeve 34 into the retracted position shown in FIGS. 2A and 2B. At the other end of inner sleeve 34, the tip 43 is chamfered so that it will register with the edges 4 of the holes 2 in miniplate 1. Instead of a chamfered tip for the inner sleeve, an alternative plate holding structure can be fashioned at the tip of the inner sleeve depending on the particular geometric characteristics of the plate involved. The barrel of inner sleeve 34 is scored with markings 44 that will enable the surgeon to gauge the length of screw required.

A lever 46 having first and second lever arms 48, 49 is mounted via hinge pin 50 on the long leg 18 of L-shaped member 14. The lever arm 48 includes a hole 51 and slot 52 arrangement by means of which lever arm 48 is mounted on the land 40 of inner sleeve 34. The hinge pin 50 is constructed in the form of a thumb screw so that it can be disassembled.

The combined surgical orbital drill guide and retractor 10 is used as follows. An incision is made in the region where the miniplate 1 is to be placed and the bones are reduced to their correct anatomical positions. The surgeon then inserts the device 10 into the incision in such a manner that the major retractor 20 and the minor retractor 26 retract the sides of the incision. At the same time, the device 10 is manipulated so that the major retractor 20 is positioned on and behind the bone to act as a protective stop there while the minor retractor 26 is straddled over the lateral aspect of the incision and any major nerve in that region. With the device 10 in place the miniplate 1 is then inserted over the reduced bone structure. Alternatively, the miniplate 1 may be positioned into place prior to insertion of the device 10 in the incision. In either event, after the miniplate 1 and the device 10 are in place, with one of his fingers the surgeon depresses the lever arm 49 so that it is brought into proximity with the handle 12. This causes the lever arm 48 to press against the shoulder 36 and the inner sleeve 34 slides forward through the bore of outer sleeve 32 and through the aperture 24 of major retractor 20 until the tip 43 abuts against a hole 3 of miniplate 1. Because the tip 43 is chamfered, it is well-fitted against the beveled edge of the hole 3 and is thus able to hold the miniplate 1 in place.

Thus, with a single hand, the surgeon is able to retract the sides of the incision, brace the miniplate in place, and provide a drill guide and protective stop behind the bone to be drilled. With the other hand, the surgeon now commences drilling by inserting a drill bit (not shown) through the longitudinal bore of the inner sleeve 34 and drilling through the bone. The drilling proceeds until the drill bit passes through the bone and reaches the tip 23 of the major retractor 20 located behind the bone. At this point, the drill bit is withdrawn and a self-tapping surgical screw is inserted through the bore of the inner sleeve 34 and screwed through the miniplate 1 and the bone. Because the markings 44 on the inner sleeve 34 are calibrated against the distance to the tip 23 of major retractor 20, the surgeon can easily determine the combined depth of the miniplate and the bone. This enables the surgeon to select a screw of the precise length required.

When this procedure is completed for one hole, the surgeon moves to the next hole of the miniplate 1 and repeats the procedure until the miniplate has been properly secured into position on the reduced bone structure.

An additional feature of the device 10 is that it is easy to disassemble. To disassemble the device 10, the thumb screw 50 is removed and lever 46 is disconnected from the leg 18 and the inner sleeve 34. Thereafter, the inner sleeve 34 and the spring 42 are removed from the leg 16.

Figures 3A, 3B:
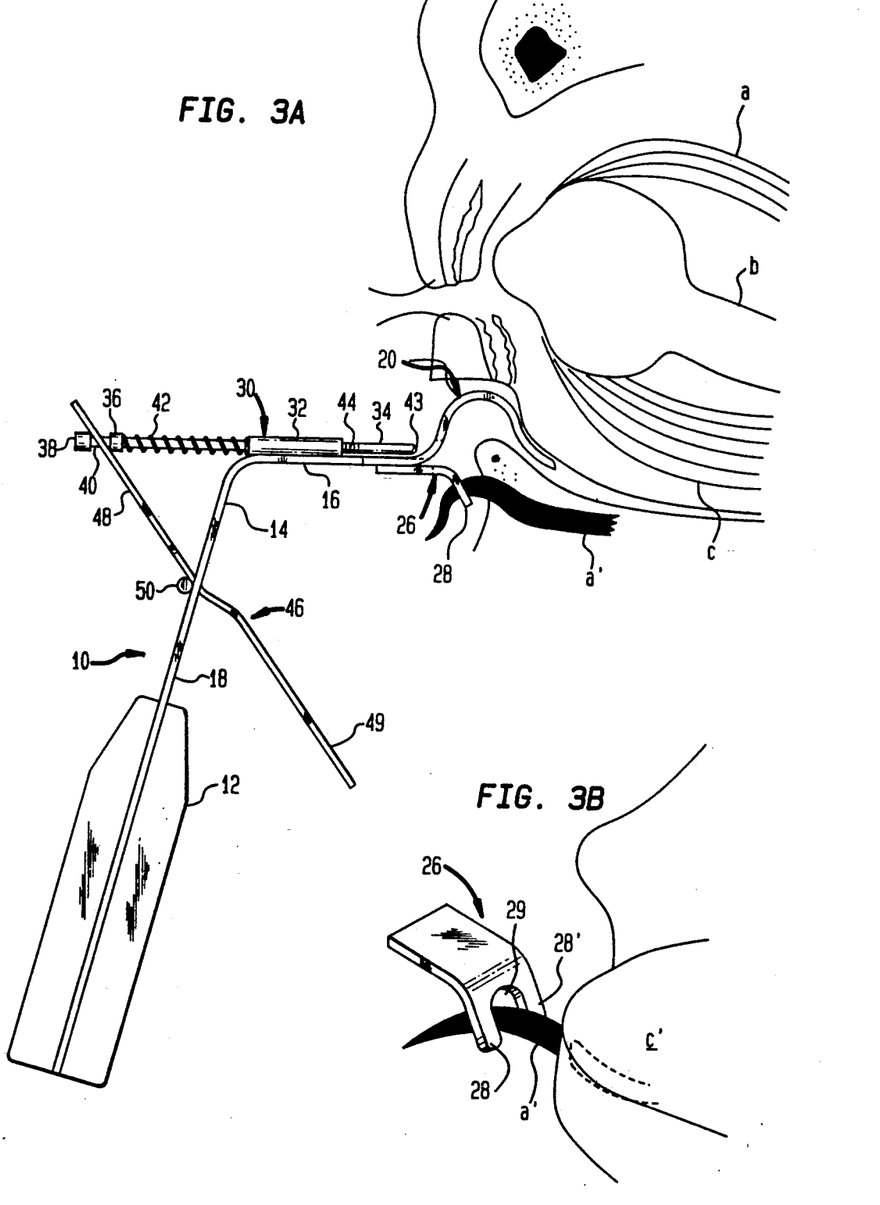
FIGS. 3A and 3B illustrate the inventive surgical drill guide and retractor in an infraorbital application.
Figure 4:
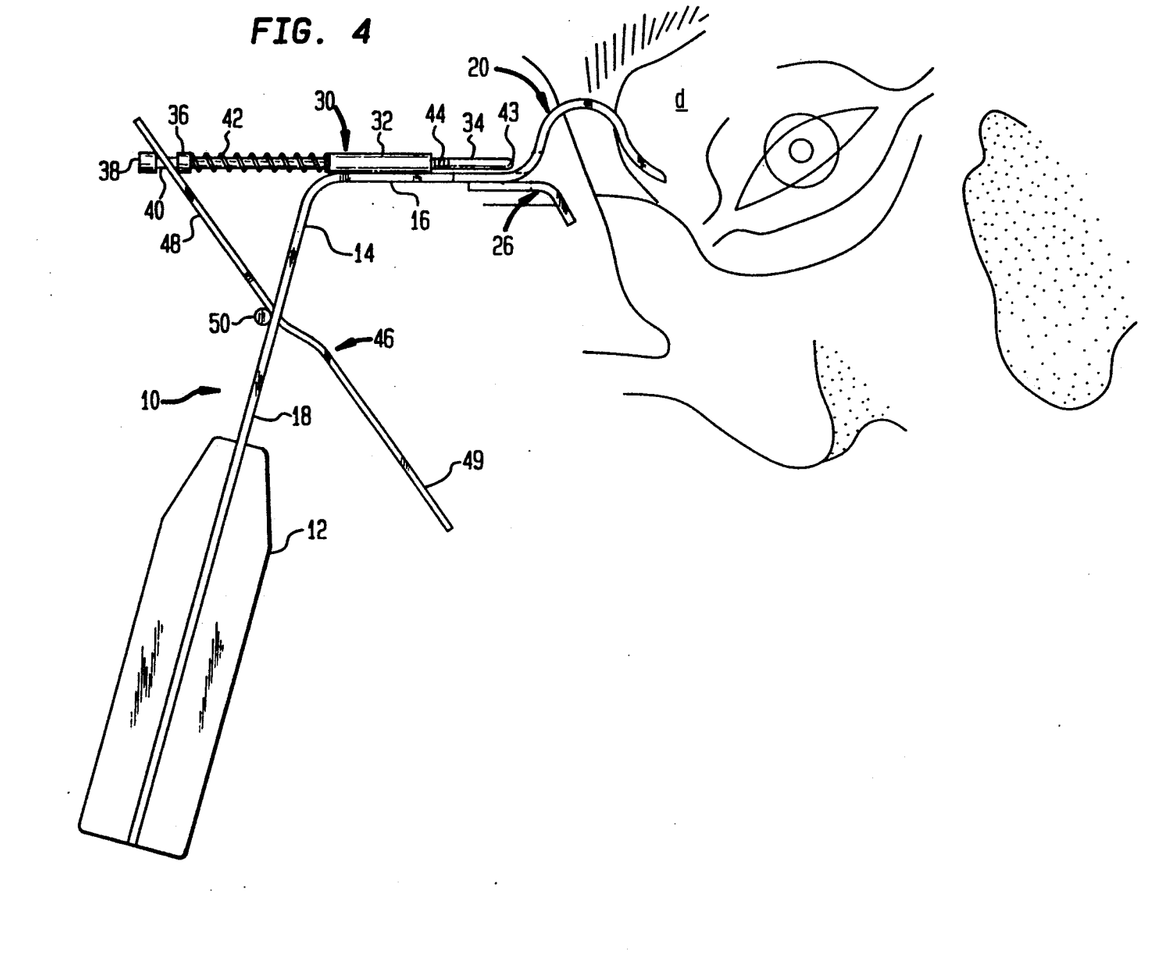
FIG. 4 illustrates the inventive surgical drill guide and retractor in a zygomaticofrontal application.

The device 10 illustrated in FIGS. 2A and 2B is primarily useful for the application of miniplate osteosynthesis to the infraorbital and zygomaticofrontal regions. FIGS. 3A, 3B and FIG. 4 respectively illustrate the use of device 10 in these regions. In FIGS. 3A and 3B, a designates the superior rectus muscle, b designates the optic nerve, and c designates the inferior rectus muscle. The infraorbital nerve is designated by a'. FIG. 3B illustrates the fingers 28 and 28' passing on either side of the infraorbital nerve in the vicinity of the infraorbital rim and the orbital floor c'. In FIG. 4, the inventive device 10 is illustrated as being used in the zygomaticofrontal region which is designated by d. In FIG. 4, the minor retractor 26 is shown retracting one side of the incision.

Figure 5:
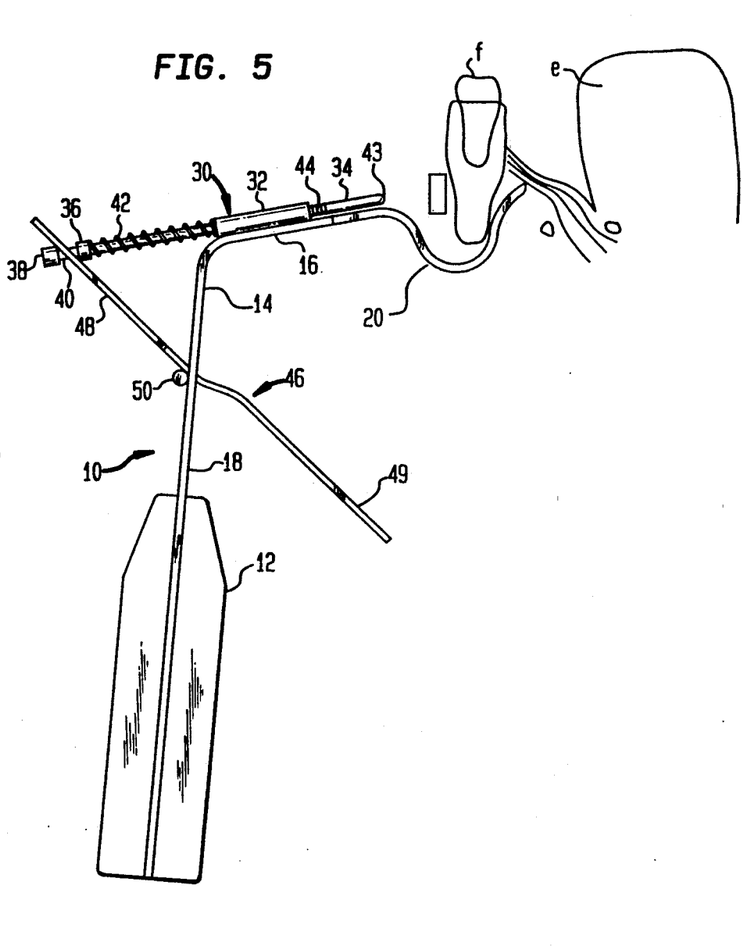
FIG. 5 illustrates an embodiment of the surgical drill guide and retractor in a mandibular application.
Figure 6:
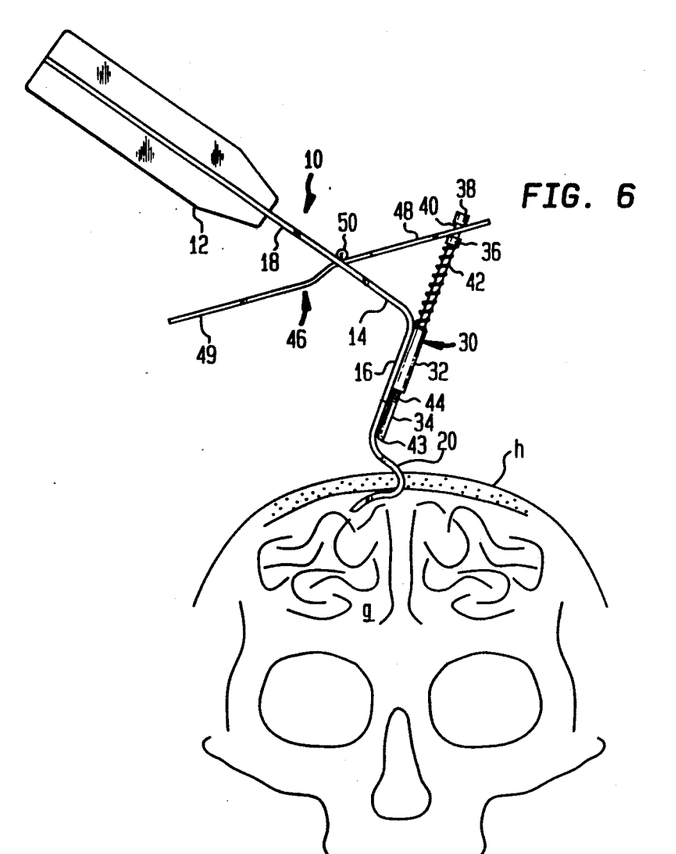
FIG. 6 illustrates an embodiment of the surgical drill guide and retractor in a cranial application.

The device 10 may also be adapted for use in the mandibular and cranial regions and such applications are illustrated in FIGS. 5 and 6 respectively. In FIG. 5, f designates the mandible in the coronal region with the tongue being shown as e. In FIG. 6, g designates the brain within the cranium h. For these applications, the minor retractor can be omitted from the device 10 since there is no need to straddle any major nerves.

Figure 7:
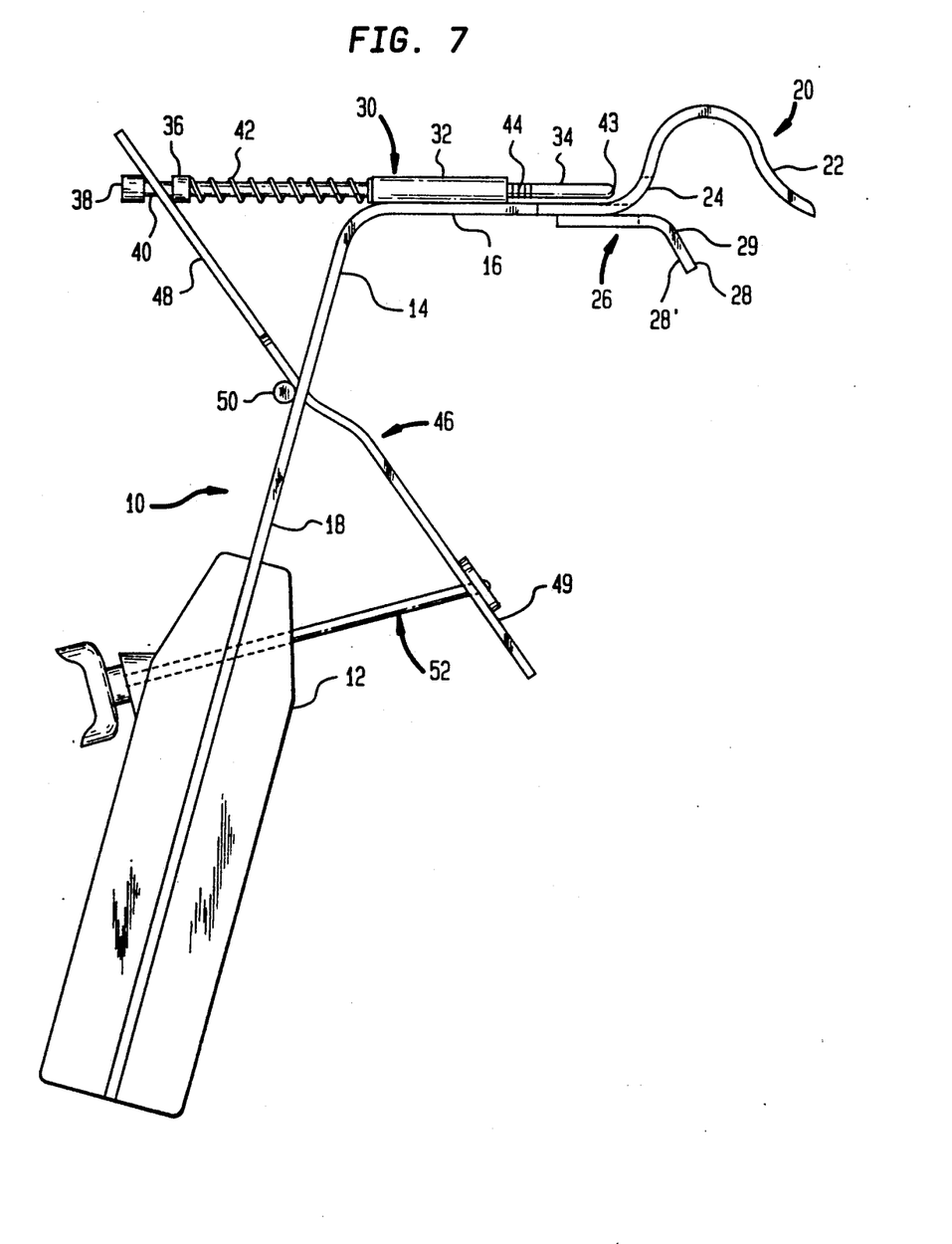
FIG. 7 illustrates another embodiment of the inventive surgical drill guide and retractor.

FIG. 7 illustrates another embodiment of the invention. In this embodiment, a wing nut mechanism 52 or other similar retaining mechanism is provided which is capable of retaining the inner sleeve 34 in its extended position without the need for the surgeon to press against lever arm 49. In this case the inventive instrument is self-retaining.

Figure 8A:
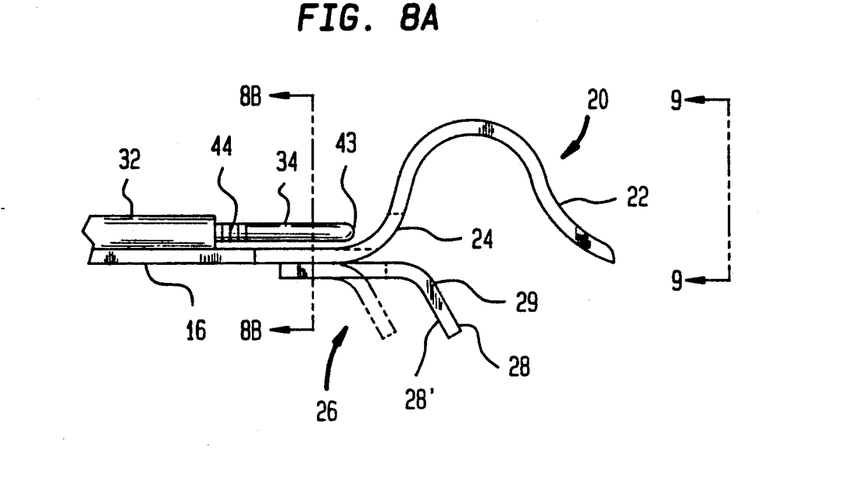
FIGS. 8A and 8B illustrate the inventive surgical drill guide with an adjustable minor retractor.
Figure 8B:
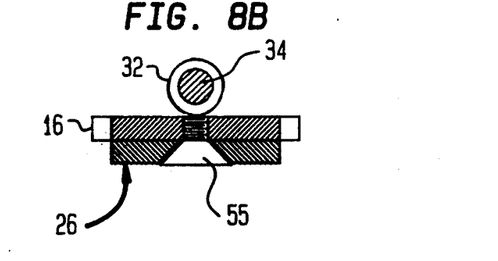

FIGS. 8A and 8B illustrate another embodiment of the invention. In this embodiment, the minor retractor 26 includes a slot (not shown) and a set screw 55. The slot and set screw 55 permit the surgeon to adjust the position of minor retractor 26 as shown in phantom in FIG. 8A. Other embodiments for making the minor retractor 26 movable relative to the leg 16 will be apparent to those skilled in the art. For example, the minor retractor 26 may be attached to leg 16 in a sliding fashion with a set screw on a lateral surface rather than on an undersurface of the minor retractor, or the minor retractor 26 may be attached to the leg 16 by a universal joint. In each of these cases, the movability of minor retractor 26 provides the surgeon with freedom to manipulate its position around major nerves and ligaments.

Figure 9:
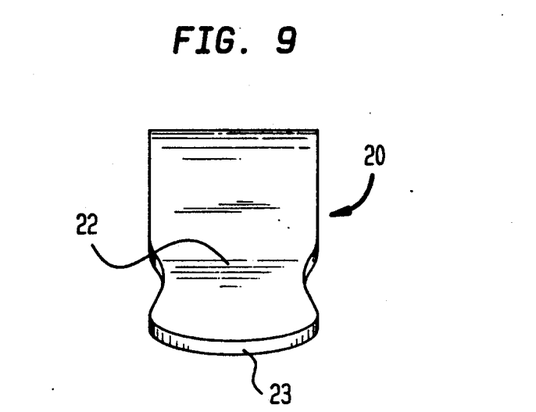
FIG. 9 illustrates the inventive surgical drill guide with a contoured major retractor.

FIG. 9 illustrates another embodiment of the major retractor 20. In this embodiment, the lateral sides of major retractor 20 are contoured with indentations in the region of concavity 22. The contoured sides allow the major retractor to avoid injuring the lateral canthal ligament.

Figure 10:
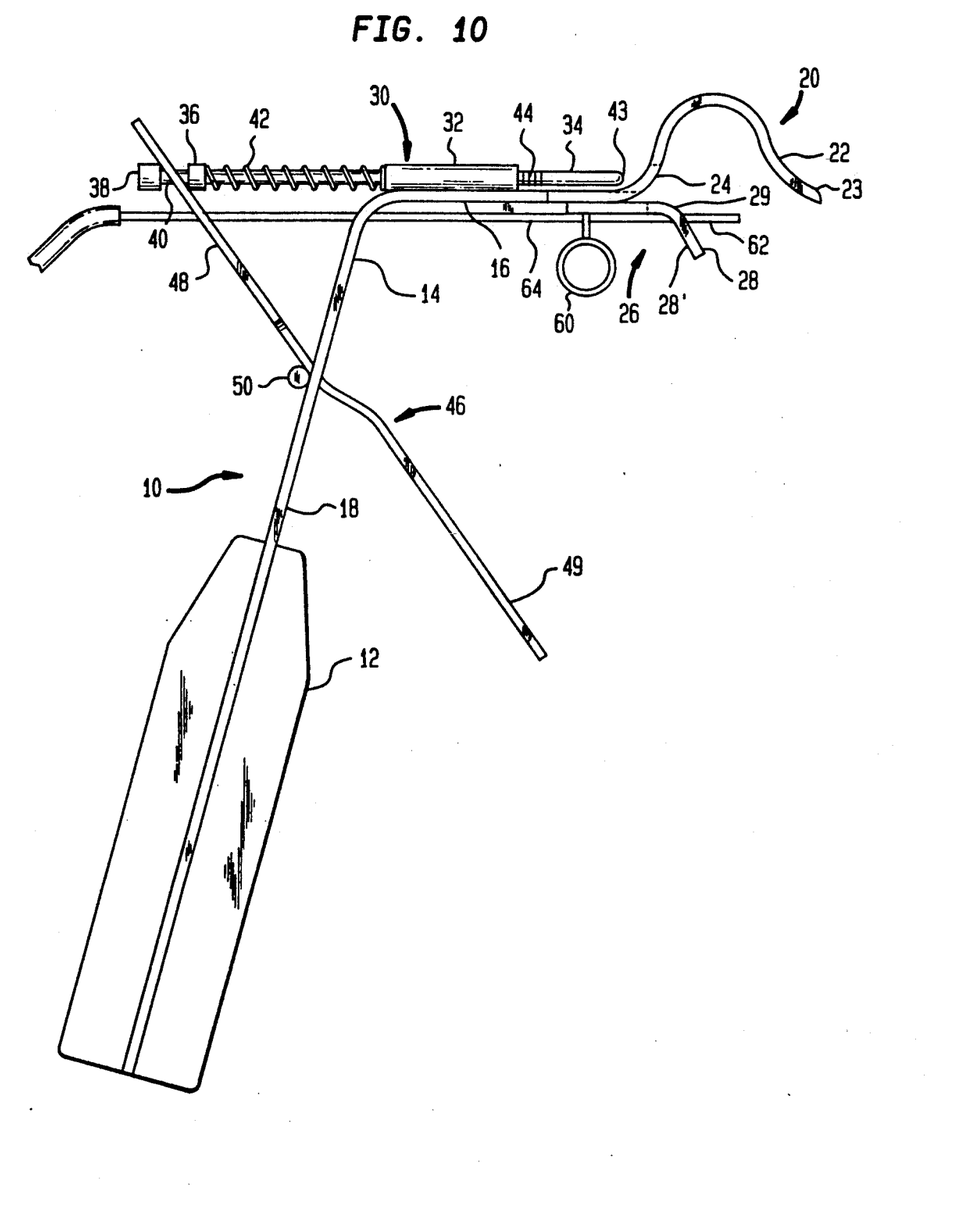
FIG. 10 illustrates another embodiment of the inventive surgical drill guide.

FIG. 10 illustrates yet another embodiment of the invention. This embodiment is similar to that shown in FIG. 2B except that two additional features have been added. The embodiment shown in FIG. 10 includes a trigger grip 60 which makes it easier to manipulate the position of minor retractor 26 with the same hand that is holding the handle. The embodiment shown in FIG. 10 also includes a suction tip 62 which protrudes between the fingers 28, 28' and extends into the gap 29. The tubing 64 for suction tip 62 runs along the undersurface of leg 16 and passes through apertures (not shown) in leg 18 and in arm 48. In other embodiments of the invention, the suction tip 62 may be located in different positions, for example, attached to major retractor 20.

The inventive surgical drill guide and retractor may be used to perform all the various steps of bone plating as follows. After creating an incision and anatomic dissection, the surgical drill guide is inserted into position either before or after reduction of the bone segments. The bone plate is then adapted correctly and a drill bit is inserted into the bore of the drill guide. A hole of the correct size is then drilled into the bone. If the drill guide is being used in the frontozygomatic or infraorbital region, then, after removal of the drill bit, a self-tapping screw is inserted into the bore of the drill guide and this is followed by the insertion of a screwdriver to tighten the screw securely. The process continues until the plate is completely screwed into place.

However, if the site of operation is in the cranium, mandible or other long bone, then after removal of the drill bit, a tap is inserted into the bore of the drill guide and is used to prepare the bone for receiving a screw. After the tap is removed, an appropriate size screw is inserted through the bore of the surgical drill guide followed by a screwdriver to tighten the screw. Prior to selection of a screw, the depth gauge on the barrel of the drill guide is used to determined the correct screw length. These steps are repeated until the bone plate is completely secured.

Desirably, the drill bit and the tap which are used to make the hole in the bone are constructed with a wide shank followed by a narrower drilling or tapping portion. The bore of the inner sleeve is of sufficient width to receive the wide shank of the drill bit and tap. This will enable it also to accommodate the wider dimension of the screw head.

It will be apparent to those skilled in the art that the inventive surgical drill guide and retractor can also be used for wire fixation in addition to rigid internal fixation with a bone plate.

While the invention has been described by the reference to specific embodiments, this was for purposes of illustration only and should not be construed to limit the spirit or the scope of the invention.

I claim:

1. A combined surgical drill guide and retractor, comprising
   a handle,
   a member attached to said handle,
   retraction means extending from said member for retracting at least one side of an incision, said retraction means being of arcuate shape so that it can be inserted into said incision and will extend around and behind a bone located in the vicinity of said incision,
   a cylindrical first sleeve mounted on said member for movement between a retracted and an extended position, said first sleeve including a through-going bore dimensioned for slidably receiving a drill bit or other instrument therethrough, and
   a lever in contact with said first sleeve, said lever having first and second arms arranged so that when said first arm is moved towards said handle, said second arm causes said first sleeve to occupy said extended position,
   wherein said first sleeve extends into said incision near the front of said bone when in said extended position.

2. The drill guide and retractor of claim 1 wherein said retraction means includes a broad tip portion for abutting against the back of said bone.

3. The drill guide and retractor of claim 2 wherein said tip portion is concave and slopes toward said incision.

4. The drill guide and retractor of claim 3 wherein said tip portion includes contoured lateral sides.

5. The drill guide and retractor of claim 1 wherein said lever is hingedly mounted for scissoring movement in cooperation with said handle and said first sleeve.

6. The drill guide and retractor of claim 5 further comprising biasing means disposed against said first sleeve for biasing said sleeve into said retracted position.

7. The drill guide and retractor of claim 1 further comprising suction means mounted on said retraction means for removing fluids when said retraction means is inserted into said incision.

8. The drill guide and retractor of claim 1 wherein said retraction means comprises a major retractor extending from said member and having an aperture disposed opposite said first sleeve so that said first sleeve can pass through said aperture in said extended position.

9. The drill guide retractor of claim 8 wherein said retraction means further comprises a minor retractor extending from said member in a direction substantially opposite to the direction at which said major retractor extends from said member, said major and minor retractors cooperating to retract opposite sides of said incision.

10. The drill guide and retractor of claim 9 further comprising means for movably mounting said minor retractor on said member.

11. The drill guide and retractor of claim 9 wherein said minor retractor includes gripping means for moving said minor retractor.

12. The drill guide and retractor of claim 9 wherein said minor retractor is bifurcated.

13. The drill guide and retractor of claim 1 further comprising a second sleeve mounted on said member, said second sleeve having a through-going bore in which said first sleeve is movably disposed.

14. The drill guide and retractor of claim 1 wherein said member is L-shaped with first and second legs, said first sleeve being mounted on said first leg, said second leg extending from said handle.

15. The drill guide and retractor of claim 1 wherein said first sleeve comprises means for clamping a fixation plate against said bone.

* * * * *